(12) United States Patent
Chichilnisky et al.

(10) Patent No.: US 9,452,289 B2
(45) Date of Patent: Sep. 27, 2016

(54) METHOD FOR IDENTIFICATION OF RETINAL CELL TYPES INTRINSIC PROPERTIES

(75) Inventors: Eduardo-Jose Chichilnisky, Cardiff, CA (US); Lauren Jepson, San Diego, CA (US); Martin Greschner, Oldenburg (DE)

(73) Assignee: Pixium Vision SA (FR)

( * ) Notice: Subject to any disclaimer, the term of this patent is extended or adjusted under 35 U.S.C. 154(b) by 138 days.

(21) Appl. No.: 14/005,818

(22) PCT Filed: Mar. 19, 2012

(86) PCT No.: PCT/US2012/029683
§ 371 (c)(1),
(2), (4) Date: Dec. 27, 2013

(87) PCT Pub. No.: WO2012/129175
PCT Pub. Date: Sep. 27, 2012

(65) Prior Publication Data
US 2014/0121724 A1 May 1, 2014

Related U.S. Application Data (60) Provisional application No. 61/454,149, filed on Mar. 18, 2011.

(51) Int. Cl.
*A61N 1/05* (2006.01)
*A61N 1/36* (2006.01)
(Continued)

(52) U.S. Cl.
CPC ......... *A61N 1/36046* (2013.01); *A61B 5/0496* (2013.01); *A61B 5/4851* (2013.01); *A61B 5/6821* (2013.01); *A61B 5/7264* (2013.01); *A61N 1/0543* (2013.01)

(58) Field of Classification Search
CPC ........... A61N 1/0543; A61N 1/36046; A61B 5/0496; A61B 5/6821
See application file for complete search history.

(56) References Cited

U.S. PATENT DOCUMENTS

| | | |
|---|---|---|
| 5,944,747 A | 8/1999 | Greenberg et al. |
| 6,432,050 B1 | 8/2002 | Porat et al. |
| 2002/0193845 A1 | 12/2002 | Greenberg et al. |

(Continued)

FOREIGN PATENT DOCUMENTS

| | | |
|---|---|---|
| JP | 2005-279002 | 10/2005 |
| WO | WO 2012/129175 | 9/2012 |
| WO | WO 2014/193990 | 12/2014 |

OTHER PUBLICATIONS

Petrusca et al, Identificaiton and Characterization of a Y-like Primate Retinal Ganglion Cell Type. The Journal of Neuroscience, Oct. 10, 2007, 27(41):11019-11027.*

(Continued)

*Primary Examiner* — William Levicky
(74) *Attorney, Agent, or Firm* — Cooley LLP (57) ABSTRACT

Retinal prostheses are configured to apply retinal stimulus signals based on retinal cell classification such as cell types or cell clusters identified based on retinal cell signals. Cell types are identified based on spontaneous or induced retinal electrical signals and analyzed based on temporal patterns of electrical activity, spatio-temporal voltage waveforms, and signal correlations that can be obtained from temporal spike patterns. Cell type indications are stored, and a signals are applied to the retina based on the stored cell type indications.

19 Claims, 8 Drawing Sheets

(51) Int. Cl.
*A61B 5/0496* (2006.01)
*A61B 5/00* (2006.01)

(56) References Cited

U.S. PATENT DOCUMENTS

| | | | |
|---|---|---|---|
| 2004/0030383 A1 | 2/2004 | Havey et al. | |
| 2005/0004625 A1* | 1/2005 | Chow | A61F 9/0017 607/54 |
| 2005/0288734 A1* | 12/2005 | Greenberg | A61N 1/0543 607/54 |
| 2006/0135862 A1* | 6/2006 | Tootle | A61B 5/04001 600/373 |
| 2008/0046031 A1 | 2/2008 | Greenberg et al. | |
| 2008/0086206 A1* | 4/2008 | Nasiatka | A61F 9/08 623/6.14 |
| 2009/0281451 A2 | 11/2009 | Hetling et al. | |
| 2010/0063498 A1 | 3/2010 | Kaushal et al. | |
| 2010/0241192 A1 | 9/2010 | Greenwald et al. | |
| 2012/0109295 A1* | 5/2012 | Fan | A61N 1/0543 623/6.63 |
| 2013/0035742 A1 | 2/2013 | Talbot et al. | |
| 2014/0375782 A1 | 12/2014 | Chichilnisky et al. | |

OTHER PUBLICATIONS

Greschner et al, Correlated tiring among major ganglion cell types in primate retina. The Jornal of Physiology, 589.1 (2011):75-86.*

Schwarz et al.: "Single Chip CMOS Imagers and flexible stimulators for a Retina Implant System", Sensors and Actuators 2000.*

International Search Report and Written Opinion for International Application No. PCT/US2014/039844, mailed Sep. 23, 2014, 16 pages.

Supplementary European Search Report for European Application No. 12760531.9, mailed Aug. 12, 2014, 7 pages.

International Search Report and Written Opinion for International Application No. PCT/US2012/029683, mailed Jul. 17, 2012, 11 pages.

* cited by examiner

METHOD FOR IDENTIFICATION OF RETINAL CELL TYPES INTRINSIC PROPERTIES

CROSS REFERENCE TO RELATED APPLICATION

This application claims the benefit of U.S. Provisional Application No. 61/454,149, filed Mar. 18, 2011, which is herein incorporated by reference in its entirety.

ACKNOWLEDGMENT OF GOVERNMENT SUPPORT

This invention was made with government support under Grant EY021271 awarded by the National Institutes of Health. The government has certain rights in the invention.

FIELD

This disclosure concerns methods for the identification of retinal cell types, and retinal prostheses that use retinal cell type identification.

BACKGROUND

A retinal prosthesis is a device implanted in the eyes of blind patients to stimulate retinal neurons that have survived degeneration, causing those neurons to transmit artificial visual signals to the brain. If the artificial visual signals closely mimic natural retinal signals, the device could provide useful artificial vision to millions of blind patients. A major limitation of prototype prostheses now in clinical trials is that they stimulate many neurons of different types indiscriminately and simultaneously. This is problematic because in the normal retina, roughly 20 different types of retinal ganglion cells send different types of visual information to diverse targets in the brain, and these cell types are intermingled in the retina. Four major ganglion cell types (ON-midget, OFF-midget, ON-parasol, OFF-parasol) form about 70% of the visual signals conveyed to the brain and supply neural signals to brain areas responsible for high resolution vision. In normal vision, these cells produce different signals at different times. For example, ON and OFF cells respond to increments and decrements of light, respectively; midget cells exhibit slower and less transient responses than parasol cells. Thus, current prostheses that activate different cell types simultaneously and indiscriminately produce abnormal retinal signals. Such a device is of limited utility to the patient.

SUMMARY

Provided herein are methods for identifying cell clusters or cell types of retinal cells at one or more areas of a retina by recording corresponding electrical signals. Based on the recorded signals, cell types or clusters are identified, and electrical stimuli are applied based on the identified cell types. In some embodiments, temporal spike patterns of the cells are recorded, and cell spatio-temporal voltage patterns and spike pattern cross-correlations are estimated. In some examples, cells types are determined based on clustering with cells having similar electrical properties. While inherent electrical signals produced by cells can be analyzed to establish cell type, in some examples, characteristic retinal cell electrical signals are produced in response to an applied electrical or optical stimulus.

Retinal stimulus apparatus comprise a signal conditioner configured to receive an electrical signal associated with a retinal area to produce a conditioned electrical signal. A signal analyzer is coupled to the signal conditioner and configured to associate the at least one retinal area with at least one retinal cell type or cluster based on the conditioned electrical signal. In some embodiments, the apparatus further includes a memory configured to store an indication of the retinal cell type, an electrode array and/or a retinal stimulus generator. In some instances, the signal conditioner is configured to receive a plurality of electrical signals associated with respective retinal areas and produce corresponding conditioned electrical signals, and the signal analyzer is configured to associate the retinal areas with associated retinal cells types based on the conditioned electrical signal. In some embodiments, the apparatus further comprises an electrode array that includes a plurality of electrodes configured to be electrically coupled to respective retinal areas and deliver corresponding electrical signals to the signal conditioner, and the signal conditioner includes a plurality of electrode amplifiers coupled to respective electrodes. In some embodiments, the signal conditioner includes a plurality of electrode switches configured to selectively couple an associated electrode to the signal analyzer. In particular examples, the apparatus further includes a retinal stimulus generator configured to provide retinal interrogation signals to the plurality of electrodes, and the conditioned electrical signals received by the signal analyzer are based on the retinal interrogation signals. In some examples, the apparatus further includes an optical stimulus generator configured so that the electrical signals associated with the retina are based an optical stimulus signal. In some embodiments, the signal conditioner includes a plurality of electrode switches configured to selectively couple an associated electrode to the signal analyzer.

In other examples, a retinal prosthesis includes an electrode array configured to be coupled to a retina, and a retinal signal generator configured to provide electrical signals to respective electrodes of the electrode array based on retinal cell types associated with the electrodes. In some embodiments, the retinal prosthesis further includes a memory coupled to the electrical signal generator, an image sensor coupled to the retinal signal generator and/or a signal analyzer coupled to the electrode array. In some examples, the memory is configured to store indicators of the retinal cell types associated with the electrodes. In one non-limiting example, the memory is configured to store indicators of two or more retinal cell types associated with at least some of the electrodes. In further examples, the retinal prosthesis includes an image sensor coupled to the retinal signal generator such that the electrical signals provided to the respective electrodes are based on an image signal provided by the image sensor. In some cases, signals provided to electrodes are not necessarily the same as image intensities, and image sensor signals are processed in order to establish suitable electrode signals. In other representative embodiments, the retinal prosthesis further includes a signal analyzer coupled to the electrode array so as to receive electrical signals from portions of the retina and identify retinal cell types associated with the portions. In one non-limiting example, the signal analyzer is configured to store indications of the identified cell types in the memory.

The foregoing and other objects, features, and advantages will become more apparent from the following detailed description, which proceeds with reference to the accompanying figures.

BRIEF DESCRIPTION OF THE DRAWINGS

FIG. 6A includes black dots corresponding to an electrical image showing the amplitude of an average voltage obtained on 512 electrodes in a hexagonal array. Numbered dots (shaded) show electrodes for which corresponding average voltage traces are shown in FIG. 6C. Trace 1 is typical of a recording from a cell body. Trace 2 is typical of dendrites around a cell body. Traces 3-5 are typical axon waveforms. Time offsets in traces 3-5 show that the voltage waveform propagates from electrode 1 toward electrode 5. Conduction velocity of this propagation is roughly 1 msec. FIG. 6B shows electrical image for two ganglion cells (black dots) and their light-sensitive regions (circled) overlapping the cell body and dendrite locations, indicating that normal light-sensitive regions can be obtained from the electrical image.

FIG. 7A shows cross-correlations between ON-parasol cells revealing a two-peaked structure reflecting its origin in gap junctions, whereas the cross-correlation function in OFF-parasol cells exhibits only one peak. FIG. 7B shows a negative correlation between ON-midget and OFF-midget cells that differs from a positive correlation between OFF-parasol and OFF-midget cells. FIG. 7C shows that degree of correlation as a function of distance between cells declines more rapidly for parasol-midget cell pairs than parasol-parasol cell pairs, and the maximum correlation between these cell types also differs. (Greschner et al, *J. Physiol.* 589:75, 2010).

FIGS. 8A-8B are plots showing cell type clustering and identification using intrinsic properties. (A) In a primate retina, ON-parasol, OFF-parasol, ON-midget and OFF-midget cells (bottom right group, top right group, bottom left group, and top left group, respectively) were identified based on light responses. See Field et al., *J Neurosci* 27:13261, 2007. The first principal component of the auto-correlation, and the axon conduction velocity, are shown for each cell. Clustering of cell types indicates that these intrinsic properties can be used for identification. However, other aspects of auto-correlation, cross-correlation and waveform can be used as well. (B) Identification with auto-correlation in adult, degenerated P23H rat reveals three cell types in one recording indicating the utility of the method in degenerated retina.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art. In some examples, operations are discussed as occurring in a common workplace, but any combination of operations and any individual operations can be performed remotely from other operations and combinations thereof via one more wired or wireless networks or using point-to-point communication.

As disclosed herein, retinal prostheses can be configured to stimulate different retinal cell types located in different retinal areas differently, based on an identified cell type or a mixture of cells types associated with some or all retinal areas. Disclosed herein are apparatus for recording electrical signals associated with retinal cells, methods for identifying retinal cell types based on analyzed electrical signals produced by or associated with the cells, and retinal prostheses capable of applying electrical signals to selected retinal areas based on cell types identified as being associated with the retinal areas.

Representative Apparatus for Identifying Retinal Cell Types

Figure 1:
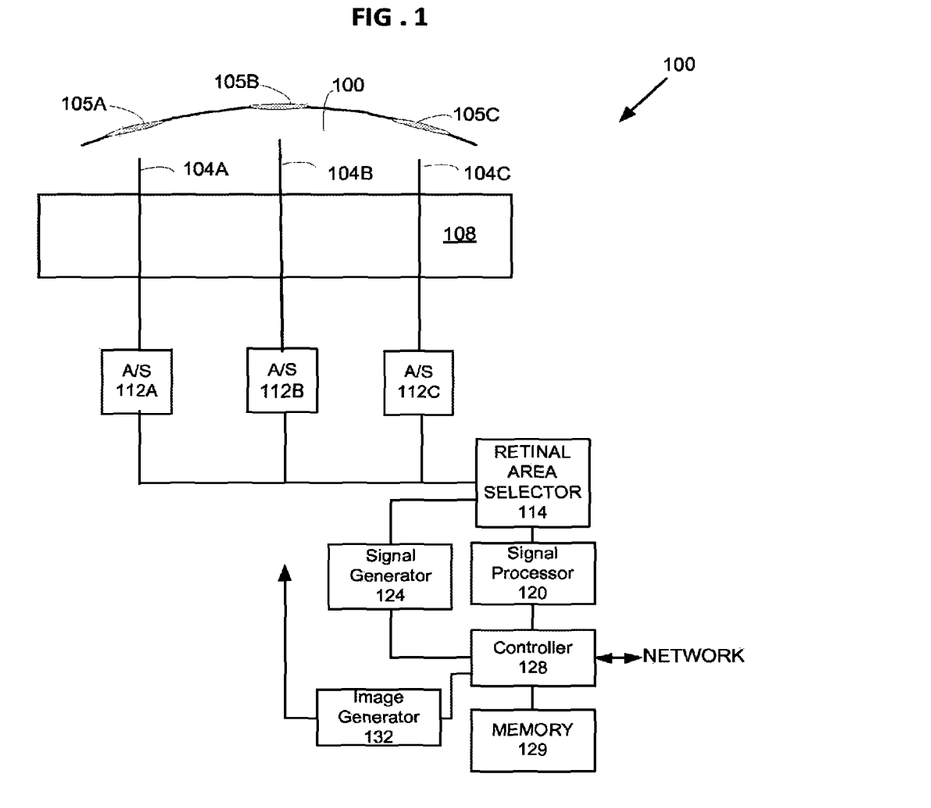
FIG. 1 is a block diagram of a representative apparatus for recording electrical signals of retinal cells, determining cell types at a plurality of electrode locations, and applying cell-type specific retinal stimuli.

With reference to FIG. 1, a representative apparatus for identifying retinal cell types at a plurality of retinal areas on a retina 100 includes a plurality of electrodes 104A-104C configured to contact or otherwise be electrically coupled to respective retinal areas 105A-105C. Only a few electrodes are shown in FIG. 1 for convenient illustration, but typically several hundreds or thousands of electrodes are used. Typically, the electrodes are arranged in patterns such as a hexagonal or rectangular array, and are retained in a substrate 108 for convenient handling.

As shown in FIG. 1, each of the electrodes 104A-104C is coupled to an associated amplifier/switch element (A/S element) 112A-112C that can be controlled so as to receive and amplify a retinal cell electrical signal, or switched so as to permit application of one or more electrical signals to the associated retinal areas. It is often convenient to include such amplifiers and switches on a single substrate that can be secured to or incorporated into the electrode substrate 108. A circuit substrate can also permit integration of other electrical functions as well as providing convenient conductors for connection to signal processing, signal conditioning, and other circuitry. The A/S elements 112A-112C can also include high pass, low pass, or band pass filters, signal buffering, and other circuit functions.

The electrodes 104A-104C are generally small enough (~10 μm) to record signals associated with individual cells and can be electroplated to have a low impedance (~100 kOhms) such that the equivalent Johnson noise during recording is low (~10 μV), but other electrodes can be used. Amplifier circuitry generally permits signal recording at sampling rates of about 20 ksample/sec (~20 kHz), and amplifier signals can be band-pass filtered (typical pass bands of ~50-2,000 Hz).

A retinal area selector 114 is coupled to the A/S elements 112A-112C so as to select one or more retinal areas from which signals are to be received at a signal processor 120 or to which signals from a signal generator 124 are to be applied. In some examples, each of the retinal areas 105A-105C is interrogated or electrically driven (stimulated) individually, while in other examples more than one retinal area is interrogated or stimulated at one time. The retinal area selector 114 can also be provided on a common substrate with the A/S elements 112A-112C. The signal processor 120 is coupled to receive amplified or otherwise conditioned electrical signals associated with the retinal areas 105A-105C. Based on the received signals, the signal processor 120 can identify one or more cell types associated with each of the retinal areas 105A-105C, determine an approximate distribution of cell types, or select a single cell type. Cell type determination is discussed in detail below.

The signal processor 120 is in communication with a controller 128 that receives cell type information, and records this information in a non-transitory storage medium 129 such as RAM, ROM, a hard disk, a flash drive, a CD ROM, or other storage media. Alternatively, cell type information can be communicated for storage, analysis, or other reasons to one or more remote servers via a local area network, a wide area network, the Internet, or point-to-point wireless connection. Wired or wireless point-to-point communications can also be used so that signal analysis, acquisition, storage, and other processes can be performed at a single location or at distributed locations. In other examples, signal data received from the retinal areas is digitized or otherwise processed by the signal processor 120 or controller 128 and stored in the memory 129. For example, retinal signals can be stored and then transmitted via a network for analysis so as to establish a corresponding cell type distribution. Such a cell type distribution can be communicated via the network for recording in the memory 129. In other examples, recorded signals are processed locally, and cell types stored in the memory 129. In addition, cell type signatures can be stored in the memory 129 based on one or more measurements, or based on common electrical signals associated with cell types. For example, electrical waveforms associated with cell types or other cell type distinguishing data or procedures can be stored. Such storage permits retinal changes to be evaluated over time, additional cell data to be used for each retinal area, or enhanced techniques to be applied.

The signal generator 124 is coupled to the retinal area selector 114 so that selected electrical signals can be applied to one or more of the retinal areas 105A-105C. For example, retinal signals to be used to determine cell type can be produced in response to electrical signals from the signal generator. This may be especially useful for retinal areas that do not produce suitable electrical signals spontaneously. In addition, the signal generator 124 can be configured to provide electrical stimuli to the retinal areas 105A-105C based on cell type information stored in the memory. An image generator 132 can also be provided to produce various images that can be directed to the retina 100 so as to optically induce cell responses which can then be measured as discussed above.

Representative Method for Identifying Retinal Cell Types

Retinal cells to be stimulated in a prosthesis can be identified as specific cell types. Alternatively, electrical signals produced by retinal cells can be evaluated so that the retinal cells be can assigned to one or more groupings, referred to herein as "clusters." In this case, specific cell types need not be identified. Cell types and cell clusters can be obtained based on temporal spike patterns, correlations of retinal electric signals, and spatio-temporal waveforms. In some examples one or both of cell typing and cell clustering can be used, and any combination of temporal spike pattern analysis, signal correlations, and spatio-temporal waveform analysis can be used for either. As used herein, "cell classification" refers to cell grouping based on either cell clusters or cell types.

In one example, cell types of retinal ganglion cells can be determined based on their recorded electrical signals. (As discussed above, in other examples, cells are clustered, and identification of cell type is unnecessary.) These electrical signals can be processed to determine, for example, temporal spike patterns, spatio-temporal voltage patterns, and correlations. Correlations and clustering of cells with similar electrical properties can be based on one or more of these patterns. In some embodiments, temporal spike patterns can be determined with recordings of 500 or more spikes, but larger numbers of spikes can facilitate analysis. In one example, such a temporal spike pattern is processed by computing an auto-correlation of a spike train. The auto-correlation shows the rate of spikes emitted by a cell as a function of time relative to occurrence of a spike at time zero, and can be used as an indicator of cell type. In other examples, spike patterns are measured by interspike interval distributions, mean vs. variance relationships, or triple correlations in order to determine cell types. Other methods of spike patterning are possible. Typical measures of spike patterning are based on the times of occurrence of spikes from a given cell during a recording.

In some embodiments, a spatio-temporal voltage pattern is obtained that can be referred to as an electrical image of the cell at a particular electrode. In one example, to obtain such an electrical image, the time of every cell spike on a selected electrode is identified, and the average voltage waveform in a time period surrounding the time of these spikes is computed for other electrodes.

In some examples, correlations such as cross-correlations between signals associated with pairs of cells are used. The cross-correlation indicates a spiking probability (or firing rate) of one cell as a function of time relative to the occurrence of a spike in a second cell. This cross-correlation indicates the degree to which different cells produce spikes independently or in a coordinated fashion. Cross-correlations may have a single peak, or two peaks depending on cell types. In addition, cross-correlations may be positive or negative, have different widths, different shapes, or differ in other aspects based on cell types.

In some embodiments, the electrical signals used for cell type identification are spontaneous retinal electrical signals. In other embodiments, the electrical signals are stimulated retinal electrical signals, such as electrically stimulated or optically stimulated signals.

Figure 2:
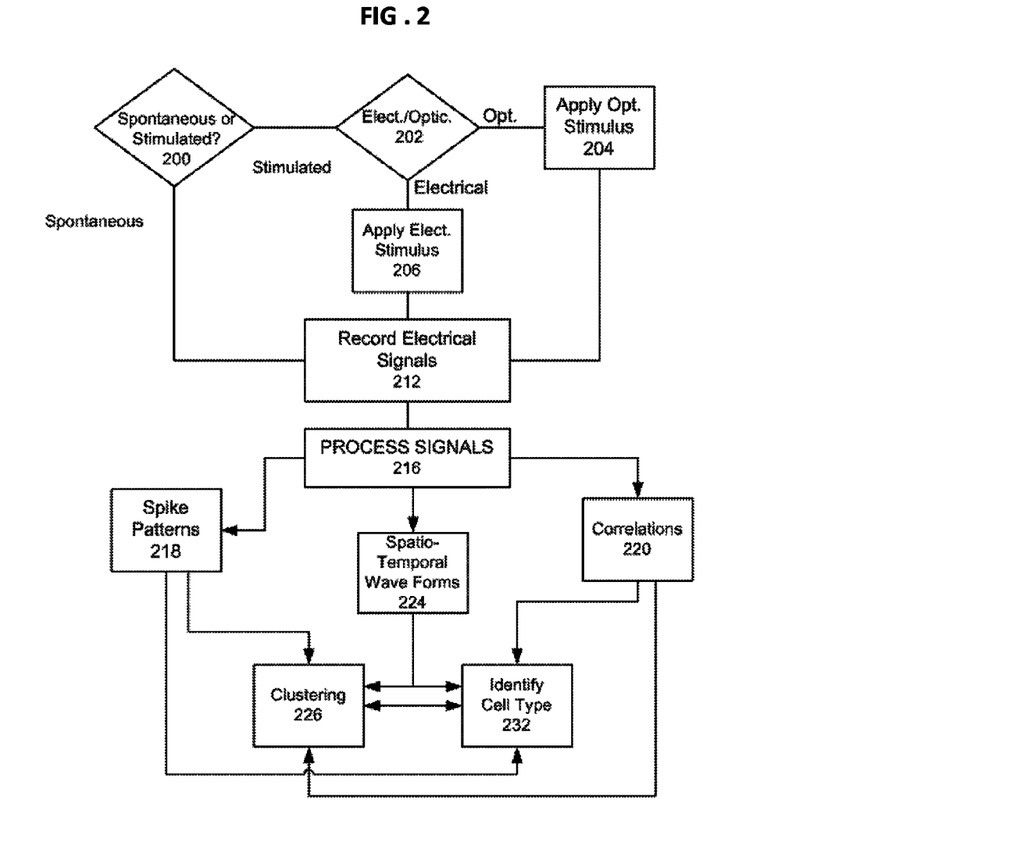
FIG. 2 is a block diagram of a method for identifying retinal cell types.

A representative method for identifying retinal cell types is shown in FIG. 2. At 200, a determination is made as to whether spontaneous retinal cell electrical signals are to be used, or if retinal cell electrical response is to be assessed based on application of a stimulus. If a stimulus is to be applied, at 202, an electrical or optical stimulus is selected, and the selected stimulus is applied at 204 and 206. At 212, electrical signals associated with one or more retina areas are detected and recorded, and in some cases, an indication of whether the retinal signals were induced (and how induced) or spontaneous is stored as well. Electrical signals associated with retinal cells in a plurality of retinal areas are generally recorded based on a retinal area to be used with a retinal prosthesis.

At 216, the recorded electrical signals are processed to establish an estimate of cell type based on a variety of approaches. For example, at 218, spike patterns can be analyzed, at 220, retinal cell signal correlations can be obtained, or at 224, spatio-temporal waveforms can be acquired. One or more of these approaches can be used to identify retinal cell types at 232. In addition, these approaches can also be used in combination with cluster analysis at 226 for cell type identification at 232. After such signal processing and analysis, the cell type identifications are generally stored or communicated. Examples that illustrate such cell type identifications are provided below, with reference to sample acquired data sets.

Representative Retinal Prostheses

Figure 3:
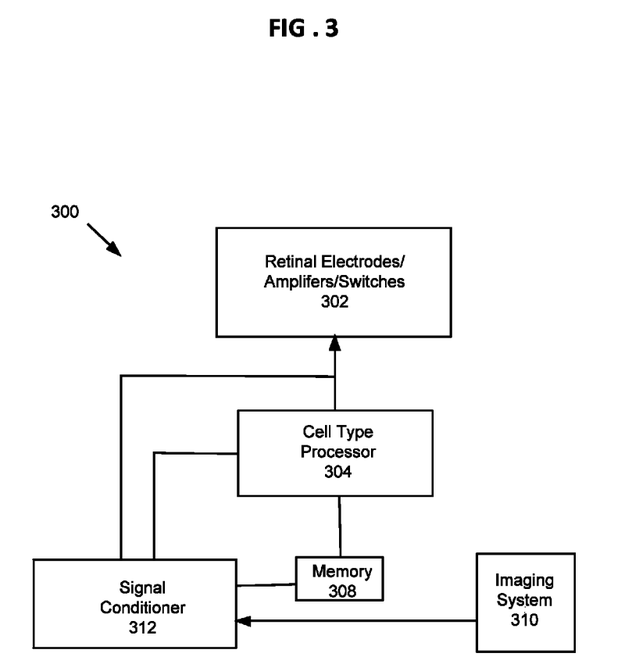
FIG. 3 is a block diagram of a representative retinal prosthesis.

With reference to FIG. 3, a representative retinal prosthesis 300 includes a plurality of retinal electrodes and associated amplifiers and switches 302 configured so that the electrodes can be placed in electrical communication with a retina. A cell type processor 304 is configured to process retinal signals from the electrode array and store cell type information in a memory 308. An imaging system is situated to produce an electrical signal associated with an image of an object in a prosthesis user field of view. The image electrical signal can be transformed as needed to provide suitable electrode stimulus signals. This electrical signal is coupled to a signal conditioner 312. Electrical signals based on retinal cell types stored in the memory 308 and the image electrical signal can be coupled to the retinal electrodes so as to produce a perceived image for the prosthesis user. The retinal electrodes can be disconnected temporarily from the signal conditioner which supplies image data to the retina during cell type determination. When disconnected from the signal conditioner, retinal electrode amplifiers can couple retinal signals to the cell type processor 304 for cell type identification. The cell type processor 304 can be configured to occasionally or periodically re-assess retinal cell types at some or all areas, and report any cell type changes that exceed predetermined limits.

The imaging system 310 can include a camera situated to produce an electrical representation of a field of view that is coupled to the signal conditioner to establish suitable retinal drive signals for some or all retina areas. The electrical representation can be a transformed representation. In some cases, the signal conditioner can supply one or more electrical signals to a particular area based on the presence of multiple cell types in the area. In some examples, only selected retinal areas receive cell-type specific stimulus signals.

Figure 4:
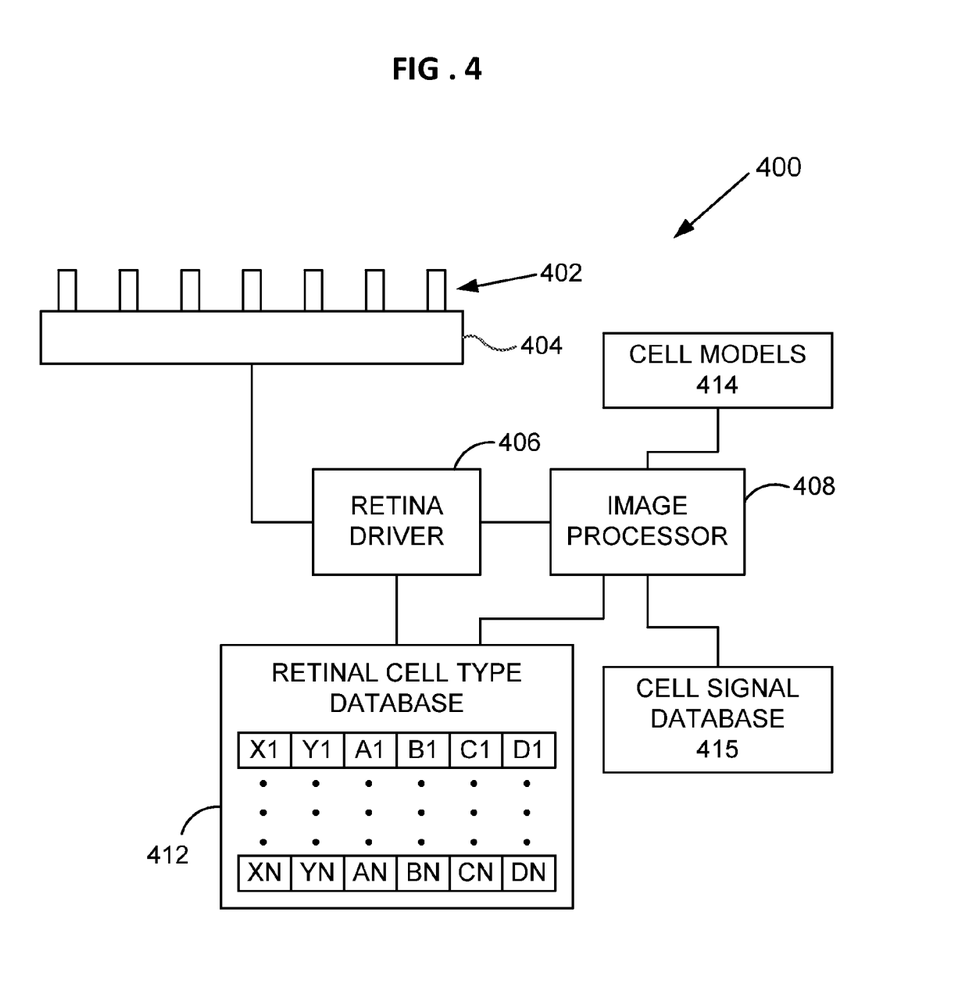
FIG. 4 is a block diagram of a representative retinal database that includes a retinal cell type database.

FIG. 4 is a further illustration of a retinal prosthesis 400. A plurality of retinal electrodes 402 are secured to an electrode signal conditioner 404 that can include electrode amplifiers as well as mechanical support for the retinal electrodes 402. The retinal electrodes 402 can be arranged in a regular hexagonal or rectangular array, randomly distributed, or otherwise arranged. A retina driver 406 is coupled to provide cell type-based retinal stimulus signals to the signal conditioner 404 and the electrodes 402 based on image data from an image processor 408. The image data can be associated with a field of view of a prosthesis user, or can be a computer-generated image or animation. In addition, signals applied to the electrodes can be dependent on current and prior images, and are not necessarily only a function of a current image.

The retina driver is coupled to a retinal cell type database 412 that includes retinal cell type indications associated with some or all of the retinal electrodes 402. In the example of FIG. 4, retinal electrode data includes location data as a coordinate pair (X,Y) and cell type fractions A-D. For example, for an electrode located at X1,Y1, proportions of cell types A-D are indicated as A1, B1, C1, D1. In some examples, only a single cell type is associated with each retinal electrode. The retina driver 406 can supply suitable drive signals to some or all retinal electrodes based on the stored cell types and the image received from the image processor 408.

Cell models can be stored in a model database 414 to provide additional information for the determination of appropriate retinal stimuli. For example, a location of a particular electrode associated with a particular cell type may not correspond to a location at which an optical stimulus would be detected in a non-degenerated retina. Accordingly, model data can provide suitable offsets so that a suitable location in an image to be perceived is selected for generation of a retinal stimulus. In addition, some or all cell types can have response patterns stored in the cell model in which cell response depends on one or more previous images in addition to or instead of a current image. The cell model for each cell may also contain other information, such as the desired timing of electrical activity of the cell or other properties specific to the cell or cell type, including those obtained from published literature on retinal cells.

Figure 6A:
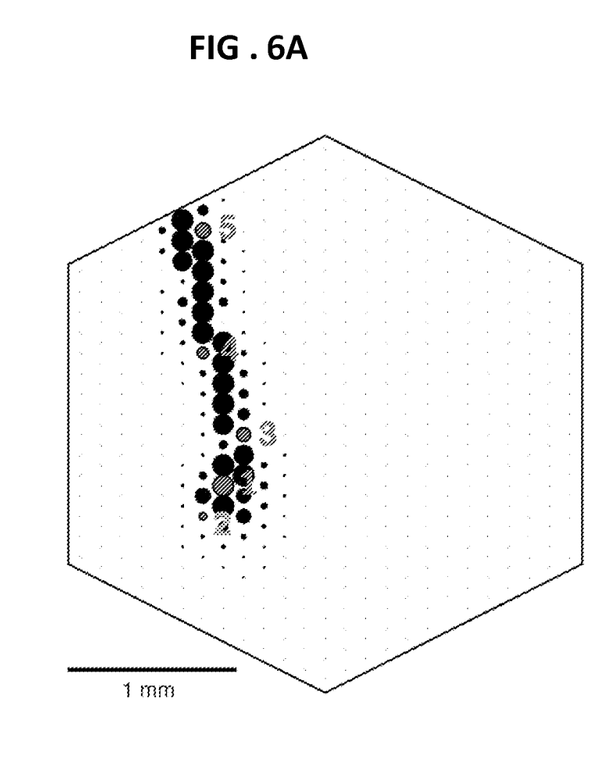
FIGS. 6A-6B are electrical images associated with retinal areas, and FIG. 6C includes associated voltage waveforms.
Figure 6B:
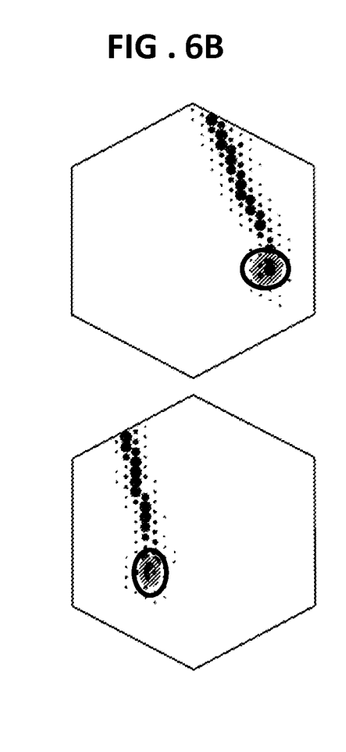
Figure 6C:
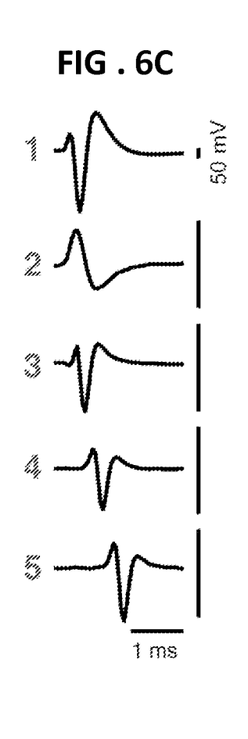

An electrical image can be used to identify the normal light-sensitive region of some or all cells. In an intact retina, each ganglion cell responds to light in a restricted region of space. When the retina has degenerated, it is generally not clear what that light-sensitive area was for each cell. In order to generate natural visual signals, each cell should be driven by a prosthesis in a way that reflects the amount of light specifically in the light sensitive region, and not necessarily the electrode location. FIGS. 6A-6B (discussed below) show that the light-sensitive regions of cells can be accurately captured by cell body and dendritic field locations obtained from an electrical image. In this way, pre-existing light-sensitive regions of each cell in the degenerated retina can be located, and this information stored and recalled for use in stimulating the cell on the basis of a visual image.

A cell signal database 415 can also be provided to store retinal drive signal information for some or all retinal cell types. For example, suitable stimulus waveforms (or parameters for generation of such stimuli), relative timings of stimulus application, or other cell-type specific stimulus characterizations can be stored in order to effectively stimulate each cell type. Signal data can be stored as waveform data or otherwise stored. If multiple cell types are associated with some electrodes, the cell signal database can also provide suitable retinal drive signal data, or indications of how signal retinal cell drive signals are to be combined. In some examples, the image processor 408 is coupled so as to receive cell type information from the database 412. In other examples, a system such as illustrated in FIG. 4 can be based on cell clusters in addition to or instead of cell types.

Electrode (X,Y) coordinates can also be used to adjust perceived images. In some cases, a particular electrode coordinate associated with a computed image location does not correspond to an image as perceived by a prosthesis user. In this case, offsets or scale factors can be applied to adjust mapping of image signals to retinal electrodes.

ADDITIONAL EXAMPLES

The following additional examples are provided to illustrate certain particular features and/or embodiments. These examples should not be construed to limit the disclosure to the particular features or embodiments described. Some examples describe methods for identifying specific retinal cell types, such as by recording cell electrical activity, and measuring activity patterns, waveforms, and correlations. Such methods can be used, for example, to identify which cells are stimulated by which electrodes in a retinal prosthesis.

Example 1

Recording

In some cases, more than one cell type is identified at a given electrode, and spikes from different cells can be segregated from one another using their waveforms, using methods such as those disclosed by Petrusca et al., *J Neurosci* 27(41):11019-11027, 2007. It is convenient to use a common electrode array to interrogate retinal areas and to apply stimulus signals but different electrode arrays such as interleaved arrays can be used. Different electrode arrays are typically selected so that inter-electrode spacing on the array is such that interrogation and stimulus electrodes can be associated with a common cell or cell type at approximately a common location.

Example 2

Spike Patterns

Figure 5:
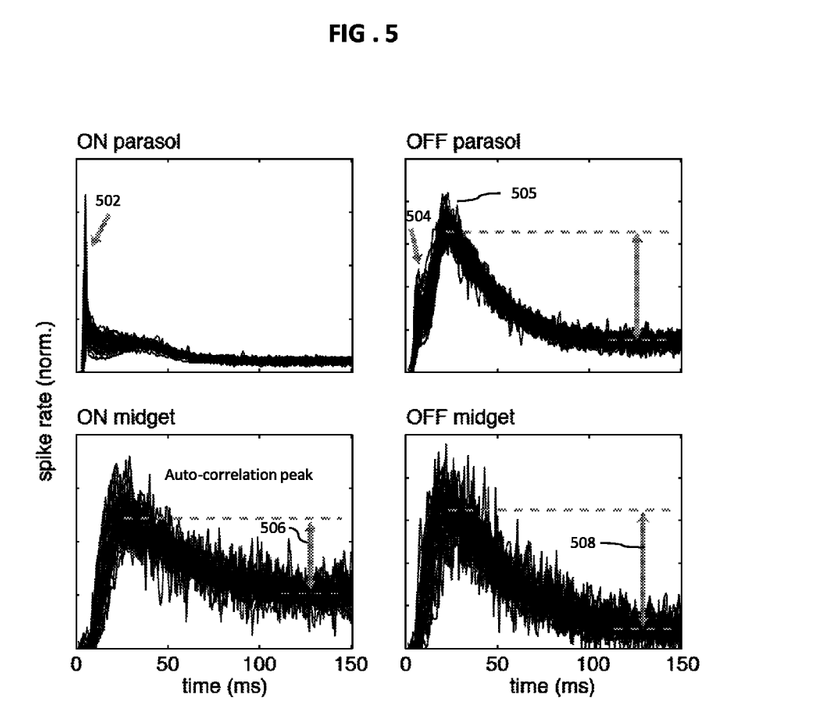
FIG. 5 is a set of graphs showing spike patterns of primate retinal ganglion measured using auto-correlations. Each panel shows the auto-correlation of the spikes of a number of cells of a particular type, recorded simultaneously from primate retina. Each trace indicates the normalized average firing rate of a cell as a function of time relative to the occurrence of a spike in the cell at time zero. Each cell type exhibits a characteristic auto-correlation waveform; traces are similar for all cells of one type (within a panel) and different for cells of different types (different panels). Arrows and lines indicate some but not all features of auto-correlation that are clearly distinct between cell types.

The temporal patterns of spikes produced by each cell are convenient for cell type identification. The spikes from different cells are generally recorded for a period of tens of minutes, such that ~10,000 spikes are recorded. From these recordings, temporal patterns of spikes produced repeatedly by the cell are determined. A simple example of a temporal pattern is two spikes separated in time by 10 ms, but many other temporal patterns are possible. An average temporal patterning of spikes produced by a given cell can be computed as an auto-correlation of the spike train. The auto-correlation shows the rate of spikes emitted by a cell as a function of time relative to occurrence of a spike at time zero. Examples of auto-correlation functions of cells recorded from macaque retina are shown in FIG. 5. Each panel shows auto-correlation functions of multiple cells of one type, superimposed. The cells of each type exhibit characteristic auto-correlation functions shapes, different from the auto-correlation function shapes of the other types. For example, in the data of FIG. 5, ON parasol cells are distinguished by a sharp peak 502 in the auto-correlation near zero. OFF-parasol cells exhibit a similar sharp peak 504 along with a broader peak 505. ON and OFF midget cells exhibit different ratios (indicated with arrows 506, 508, respectively) of the peak of the auto-correlation to its value for long time offsets.

Other measures of spike patterning are also possible: e.g. spike rate, interspike interval distributions, mean vs. variance relationships, or triple correlations. A measure of spike patterning can be any number calculated from the times of occurrence of spikes from a given cell during a recording. The auto-correlation is a general measure, but other such measures may be used in the same way. When computing a measure of patterning, such as auto-correlation (a function of time), it is convenient to summarize the waveforms for many cells by a single number for each cell. In this case, the principal components of the function are calculated, and for each cell the projection (dot product, inner product) of that cell's function is extracted onto the a selected principal component (e.g. see FIGS. 8A-8B). This is also known as the principal value for that cell.

Example 3

Spatio-Temporal Waveforms

The spatio-temporal pattern of voltage recorded on many electrodes in the array during a spike from one cell can also be used to identify distinct cell types. This may be obtained with a dense electrode array, or with smaller or less dense arrays, such as may be used in lower resolution prostheses. The spatio-temporal voltage pattern generated by a spike is measured by calculating an electrical image. To obtain an electrical image, the time of every spike of a neuron recorded on one electrode (reference electrode) is identified, and the average voltage waveform in the time period surrounding the time of these spikes is computed for all other electrodes as described by Petrusca et al., *J Neurosci* 27(41): 11019-11027, 2007. This approach includes electrodes for which each spike generates a weak signal, but averaging over many spike times on the reference electrode results in a reliable measurement that exceeds noise. An example of such an electrical image is shown in FIGS. 6A-6B.

Figure 8A:
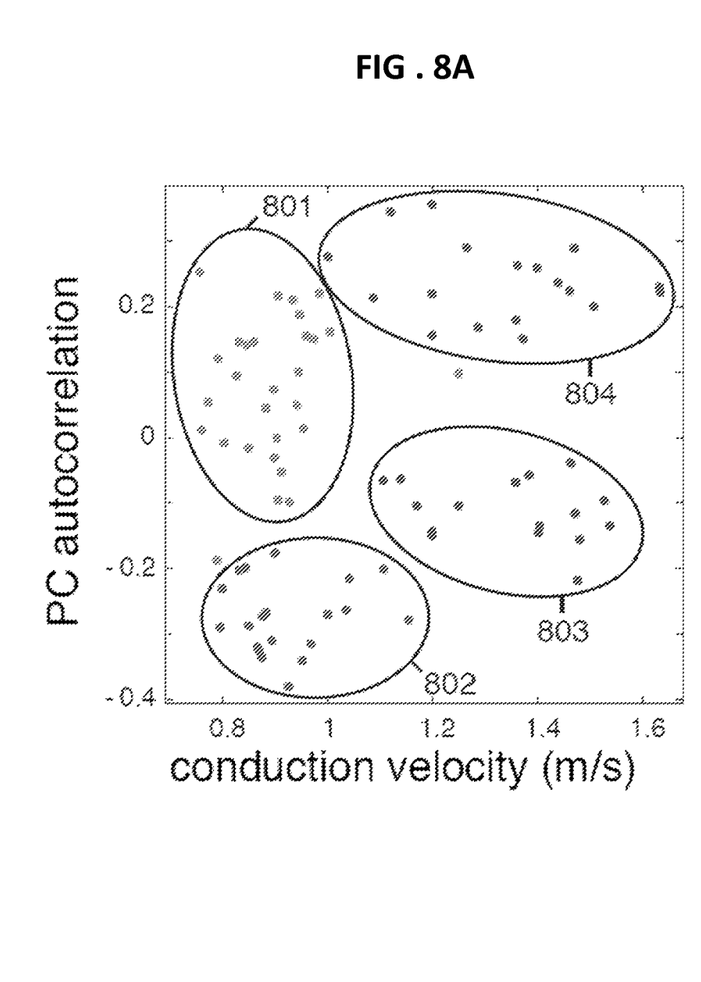

From the electrical image, specific information that is helpful in identifying different cell types can be calculated. For example, triphasic waveforms characteristic of a spike traveling down an axon may be identified on several electrodes (FIG. 6A). The spatial separation between electrodes divided by the time difference between these waveforms reveals the conduction velocity of the spike along the axon, the part of the cell that conducts spikes over long distances. This conduction velocity is known to be a characteristic of different cell types and can be used to distinguish different cell types in primate retina as shown in FIG. 8A. Other aspects of the electrical image can yield information that distinguishes cells. For example, the overall size of the electrical image (extent of cluster of electrodes around the reference electrode) can be used to distinguish parasol and midget cells from larger cell types.

Example 4

Correlations

Figure 7A:
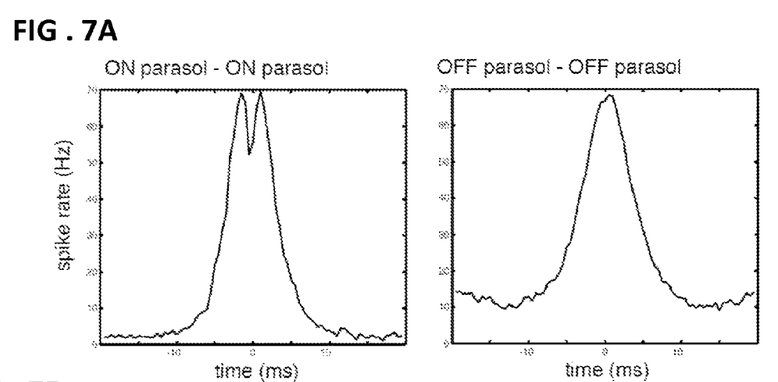
FIGS. 7A-7C are a series of graphs showing cross-correlations between identified cell types in primate retina. Each cross-correlation function indicates the spike rate of one cell as a function of time relative to the occurrence of a spike in the second cell.
Figure 7B:
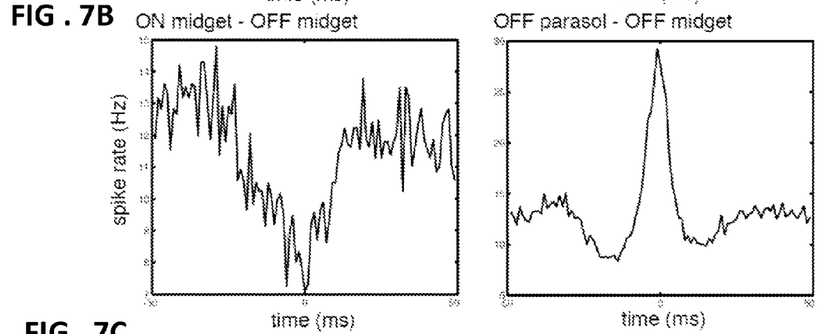
Figure 7C:
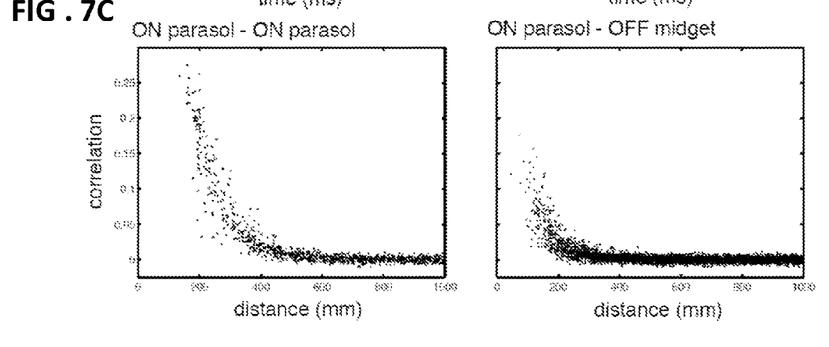

The correlation in activity of different cells, i.e. their tendency to fire in temporal relation to one another, can also be used in identifying distinct cell types. A convenient measure is a cross-correlation between pairs of cells. The cross-correlation indicates the spiking probability (or firing rate) of one cell as a function of time relative to the occurrence of a spike in a second cell and indicates a degree to which different cells produce spikes independently or in a coordinated fashion. In primate retina, cells of similar and different types exhibit characteristic cross-correlations (Greschner et al., *J Physiol* 589(Pt 1):75-86, 2010). As shown in FIG. 7A, cross-correlations may have a single peak, or two peaks depending on the cell types, reflecting the underlying mechanism. In addition, as shown in FIG. 7B, cross-correlations may be positive or negative, depending on the cell types. Generally, ON cells have positive correlation with ON cells, and OFF cells have positive correlation with OFF cells, but ON cells are negatively correlated with OFF cells. Cross-correlation magnitude declines with distance between cells differently for different cell types as shown in FIG. 7C. Also visible in the data of FIGS. 7A-7B are the characteristic forms and magnitude of cross-correlations for each cell type, as well as the fact that cross-correlations within a cell type are left-right symmetric (FIG. 7A), whereas cross-correlations between different cell types tend to be asymmetric (FIG. 7B).

Example 5

Clustering

Figure 8B:
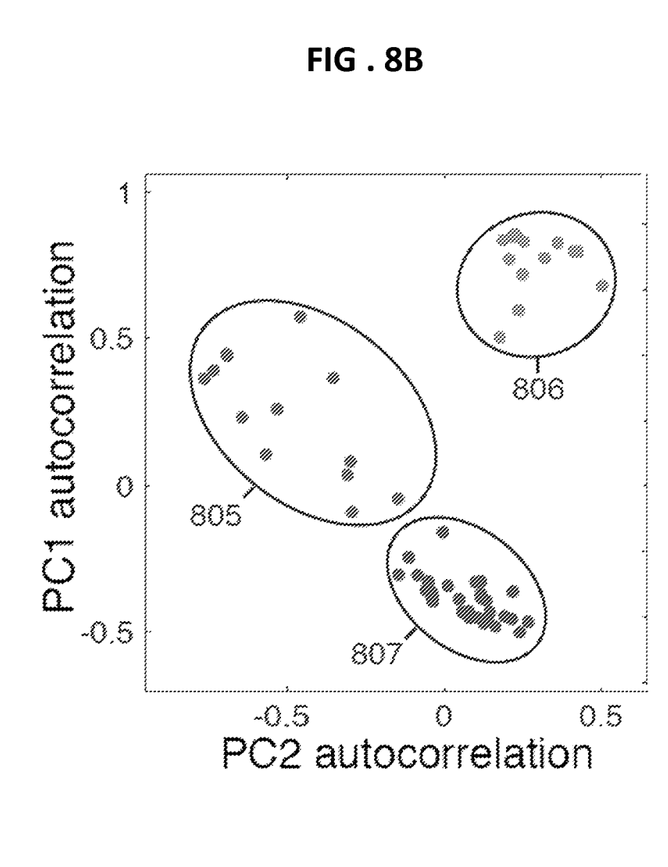

Once spike patterns, waveforms and correlation have been calculated, their distinct properties may be used to separate distinct ganglion cell types into different groups. FIG. 8A shows an example in which the auto-correlation and conduction velocity are clearly distinct for different cell types, permitting groups 801-807 to be identified. Thus, these parameters define groups of cells that are more similar to one another than to cells in different groups. An important consideration may be whether these properties of cells may change during degeneration. However, as noted above, even if cell properties change, such changes can be assessed and cell type information updated. FIG. 8B shows that in a rat model of degeneration, distinct cell types continue to segregate clearly according to their spike patterns. Waveform information from the electrical image can also be used, for example, as cells of different types typically generate spikes with different amplitudes, and have different conduction velocities. The clustering defines groups of cells that are all of the same type. Even without any further steps this can be useful, in stimulating all cells of a selected type to test what kinds of visual percepts the different types elicit, or to create a homogeneous spatial pattern of activity within one cell type which may be more interpretable to the patient than simultaneous, potentially conflicting information in many different types.

Example 6

Identification

Once the cell types are segregated from one another, cell types can be determined. In the plot of FIG. 8A, the positions of the distinct clusters are consistent across retinas and indicative of cell type. For example, parasol cells systematically exhibit greater conduction velocity than midget cells, consistently across retinas. Similarly, the autocorrelation structure of the different cell types is consistent across retinas. Although there could be some changes of these features of different cell types during retinal degeneration, some aspects of these data are expected to remain constant. For example, differences in conduction velocity are expected to remain constant during degeneration. Given that cells have already been grouped into distinct types, additional information is available about the identity of cell types in the cross-correlation. For example, the two-peaked cross-correlations for each pair of ON-parasol cells (FIG. 7A) reflects gap junction coupling, permitting a robust distinction between ON-parasol and OFF-parasol cells. Again, this is unlikely to change with degeneration. The waveforms of electrical images for each cell are also useful in identification. By examination of the waveform (FIG. 6A), an electrode is closest to the cell body of a cell can be identified (as opposed to an axon or dendrite). This in turn can be used to compute the density of cells, which can also be used as an indicator of cell type.

Example 7

Prosthesis Calibration

A computer system or dedicated processor system can be provided with computer-executable instructions to identify cell types at one or more electrodes and store such identity in one a non-transitory computer readable medium such as RAM, ROM, or on a hard disk. Cell type data can be stored on a removable medium and then coupled to a prosthesis so that the prosthesis need not include cell type identification processing. Associated cell type signals or representations thereof can also be stored. Data can be communicated via a wired or wireless network.

Example 8

Light Sensitive Regions

The electrical image can be used to identify the normal light-sensitive region of each cell. In the intact retina, each cell responds to light in a restricted region of space. When the retina has degenerated, it is generally not clear exactly what the location or extent of the light-sensitive area originally was for each cell. This can be important because, in order to generate natural visual signals, each cell should typically be driven by the prosthesis in a way that reflects the amount of light specifically in that region. FIG. 6B shows that the light-sensitive regions of cells are accurately captured by the cell body and dendritic field locations obtained from the electrical image. This method can therefore be used to determine the pre-existing light-sensitive region of each cell in the degenerated retina, information which can be used in stimulating the cell on the basis of the visual image. This method may be particularly useful in cases in which retinal cells are stimulated by electrodes at their axons, which may be at a distance from the cell body.

Example 9

Additional Prosthesis Configurations

Some prostheses may stimulate retinal cells with light and/or light-activated genetically engineered proteins, but cell type information remains useful, and an electrical recording/processing module may be provided. Additionally, electrical recording could be useful in applications such as determining which cell types remain alive in a disease like glaucoma, where ganglion cells die, or in other applications in which a degenerated retina is evaluated.

In view of the many possible embodiments to which the principles of the disclosed technology may be applied, it should be recognized that the illustrated embodiments are only preferred examples and should not be taken as limiting the scope of the disclosure. We claim as our invention all that comes within the scope and spirit of the appended claims.

We claim:

1. A method, comprising:
   receiving electrical signals corresponding to a plurality of retinal locations;
   processing the electrical signals using a signal analyzer, the processing including identifying cell types of retinal cells associated with the plurality of retinal locations;
   storing indications of the cell types within a memory wherein each of the cell types corresponds to at least one of a plurality of different cell types;
   applying, by a retinal driver, retinal stimulus signals to the plurality of retinal locations based on the identified cell types; and
   adjusting timing of ones of the retinal stimulus signals based on the identified cell types.

2. The method of claim 1, wherein the identifying the cell types includes recording temporal spike patterns at the plurality of retinal locations and processing the spike patterns to determine cell types.

3. The method of claim 2, wherein the spike patterns are processed based on spike pattern clustering to determine cell types.

4. The method of claim 1, wherein the identifying the cell types includes obtaining retinal signals from a plurality of locations, and estimating retinal cell types at the plurality of locations based on cross-correlations of the obtained retinal signals.

5. The method of claim 4, wherein the retinal cell types are estimated based on clustering of correlations.

6. The method of claim 1, wherein the cell types are identified based on cell spatio-temporal voltage patterns and wherein at least one of the indications is indicative of proportions of different types of cells associated with one of the plurality of retinal locations.

7. The method of claim 6, wherein the cell types are identified by clustering based on cell spatio-temporal voltage patterns.

8. The method of claim 1, wherein the cell types are identified based on clustering of one or more of retinal signal correlations, temporal spike patterns, or spatio-temporal waveforms or combinations thereof.

9. A method, comprising:
   receiving electrical signals from a plurality of retinal electrodes;
   processing, by a signal analyzer, the electrical signals wherein the processing includes identifying locations of light sensitive regions of a plurality of retinal cells associated with respective retinal electrodes;
   determining portions of an image to be associated with the locations of the light sensitive regions; and
   applying retinal stimulus signals to the retinal electrodes wherein each of the retinal stimulus signals is associated with one of the portions of the image wherein the retinal stimulus signals are based on a current image and at least one prior image.

10. The method of claim 9, wherein the retinal stimulus signals are based on retinal cell classifications at respective electrodes.

11. The method of claim 10, wherein the retinal cell classifications include at least one of cell types and cell clusters.

12. An apparatus, comprising:
   a signal conditioner configured to receive electrical signals corresponding to a plurality of retinal locations;
   a signal analyzer coupled to the signal conditioner and configured for processing the electrical signals, the processing including identifying cell types of retinal cells associated with the plurality of retinal locations;
   a memory for storing indications of the cell types wherein each of the cell types corresponds to at least one of a plurality of different cell types; and
   a retinal driver configured to apply retinal stimulus signals to the plurality of retinal locations based on the identified cell types wherein timing of ones of the retinal stimulus signals is adjusted based on the identified cell types.

13. The apparatus of claim 12 wherein the signal analyzer is further configured to record temporal spike patterns at the plurality of retinal locations and process the spike patterns to determine cell types.

14. The apparatus of claim 13 wherein the signal analyzer is further configured to process the spike patterns based on spike pattern clustering to determine cell types.

15. The apparatus of claim 12 wherein the signal analyzer is further configured to obtain retinal signals from a plurality of locations and to estimate retinal cell types at the plurality of locations based on cross-correlations of the obtained retinal signals.

16. The apparatus of claim 15 wherein the signal analyzer is further configured to estimate the retinal cell types based on clustering of correlations.

17. The apparatus of claim 12 wherein the signal analyzer is further configured to identify the cell types based on cell spatio-temporal voltage patterns and wherein at least one of the indications is indicative of proportions of different types of cells associated with one of the plurality of retinal locations.

18. The apparatus of claim 12 wherein the signal analyzer is further configured to identify the cell types based on clustering of one or more of retinal signal correlations, temporal spike patterns, or spatio-temporal waveforms or combinations thereof.

19. An apparatus, comprising:
   a signal conditioner configured to receive electrical signals from a plurality of retinal electrodes;
   a signal analyzer coupled to the signal conditioner and configured for (i) processing the electrical signals wherein the processing includes identifying locations of light sensitive regions of a plurality of retinal cells associated with respective retinal electrodes, and (ii) determining portions of an image to be associated with the locations of the light sensitive regions; and
   a retinal driver configured to apply retinal stimulus signals to the retinal electrodes wherein each of the retinal stimulus signals is associated with one of the portions of the image and wherein the retinal stimulus signals are based on a current image and at least one prior image.

* * * * *

UNITED STATES PATENT AND TRADEMARK OFFICE
CERTIFICATE OF CORRECTION

PATENT NO. : 9,452,289 B2  
APPLICATION NO. : 14/005818  
DATED : September 27, 2016  
INVENTOR(S) : Chichilnisky et al.

Page 1 of 1

It is certified that error appears in the above-identified patent and that said Letters Patent is hereby corrected as shown below:

On the Title Page

Item (75) should read:  
Eduardo-Jose Chichilnisky, Cardiff, CA (US);  
Lauren Jepson, San Diego, CA (US);  
Martin Greschner, Oldenburg (DE);  
Alan M. Litke, Ferney-Voltaire (FR)

Signed and Sealed this  
Thirty-first Day of December, 2019

Andrei Iancu  
*Director of the United States Patent and Trademark Office*

UNITED STATES PATENT AND TRADEMARK OFFICE
CERTIFICATE OF CORRECTION

PATENT NO. : 9,452,289 B2
APPLICATION NO. : 14/005818
DATED : September 27, 2016
INVENTOR(S) : Chichilnisky et al.

Page 1 of 1

It is certified that error appears in the above-identified patent and that said Letters Patent is hereby corrected as shown below:

On the Title Page

Item (73) Assignee, "Pixium Vision SA (FR)" should read –Salk Institute for Biological Studies, La Jolla, CA (US); The Regents of the University of California, Oakland, CA (US)–

Signed and Sealed this
Second Day of June, 2020

Andrei Iancu
*Director of the United States Patent and Trademark Office*